United States Patent [19]

McCabe

[11] Patent Number: 5,259,397
[45] Date of Patent: Nov. 9, 1993

[54] FOAM COUNTERPRESSURE GARMENT

[76] Inventor: Francis J. McCabe, 239 Hastings Ct., Doylestown, Pa. 18901

[21] Appl. No.: 607,994

[22] Filed: Nov. 1, 1990

[51] Int. Cl.$^5$ .............................................. A61B 19/00
[52] U.S. Cl. .................... 128/897; 128/882; 602/23; 602/75
[58] Field of Search ............ 602/23, 62, 13, 75, 602/78; 128/882, 897; D16/20, 15

[56]  References Cited

U.S. PATENT DOCUMENTS

| | | | |
|---|---|---|---|
| 1,775,714 | 9/1930 | Boss | 602/62 |
| 1,858,162 | 5/1932 | MacNamee | 606/62 |
| 3,744,053 | 7/1973 | Parker et al. . | |
| 3,823,712 | 7/1974 | Morel . | |
| 3,856,008 | 12/1974 | Fowler et al. | 606/62 |
| 3,933,150 | 1/1976 | Kaplan et al. | 128/DIG. 20 |
| 3,993,056 | 11/1976 | Rabischong et al. . | |
| 4,039,039 | 8/1977 | Gottfried . | |
| 4,276,341 | 6/1981 | Tanaka . | |
| 4,325,148 | 4/1982 | Livernois . | |
| 4,455,683 | 6/1984 | Moretti . | |
| 4,458,363 | 7/1984 | Harvey . | |
| 4,531,516 | 7/1985 | Poole et al. . | |
| 4,624,248 | 11/1986 | Poole et al. . | |
| 4,700,407 | 10/1987 | Mattila . | |
| 4,739,752 | 4/1988 | Cohen | 128/882 |
| 4,946,453 | 8/1990 | Monson . | |
| 4,966,134 | 10/1990 | Brewer | 128/882 |

OTHER PUBLICATIONS

"Pneumatic Anti-Shock Garment: State of the Art 1988" Annals Emerg Med May 1988; 17:506-525.
"Effect of the Pneumatic Antishock Garment on Intramuscular Pressure", Chisolm, C. D., Clark D. E., Ann, Emerg. Med. Aug. 1984; 13 581-583.
A portion of Emergency Medicine comprising the cover sheet and an article entitled "Outside Pressure for an Inside Bleed."
Gladiator Shock Suit, Antishock Pants Armstrong Medical Ind., Inc. Catalogue #112, 1988 & attached written materials relating thereto.
MAST Medical Anti-Shock Trousers- Three Styles Armstrong Medical Ind., Inc., Catalogue #112, p. 85 & attached written material relating thereto.

*Primary Examiner*—Lee S. Cohen
*Assistant Examiner*—Brian L. Casler
*Attorney, Agent, or Firm*—Ezra Sutton

[57]  ABSTRACT

A bladder-less counterpressure garment primarily used in the treatment of a victim suffering from hypovolemic shock. The garment is made of a compressible material, like foam, with a device for compressing the material. The garment is adapted to be positioned about the legs and abdomen of the victim by an adjustable fastener. The adjustable fastener or a separate pressure engagement device is engaged, compressing the foam and supplying the requisite counterpressure to increase blood circulation to the vital organs.

12 Claims, 4 Drawing Sheets

FOAM COUNTERPRESSURE GARMENT

BACKGROUND OF THE INVENTION

1. Field of the Invention

This invention relates generally to body treatment care and specifically to garments used in emergency treatment of victims suffering from hypovolemic shock and in the presence of intractable bleeding.

2. Description of the Prior Art

Shock is a life threatening condition that results when the body is unable to maintain circulation to the heart, lungs and brain. It may be caused by trauma, blood loss, toxins or other circulatory diminishment. In addition to the routine shock first-aid of lying the victim prone with the lower extremities raised to move blood to the critical organs, it is also known to apply surface counterpressure to the lower extremities sufficient to overcome the pressure in the capillary and venus system to force increased circulation to the critical organs.

Circumferential pneumatic counterpressure (CPC) devices are well known inflatable garments used to apply pressure around the arms, legs and/or abdomen to control intractable bleeding and ameliorate shock. Examples of such devices are described in U.S. Pat. No. 3,933,150 issued Jan. 20, 1976, to Kaplan et al., and U.S. Pat. No. 4,039,039 issued Aug. 2, 1977, to Gottfried. The application of a CPC device causes a dramatic circulatory rearrangement of the blood within a victim's body. The victim's blood pressure rises and the volume of blood available to the heart, lungs and head is greatly increased, while the amount of blood in the lower extremities is decreased.

The safety of CPC devices has been questioned because of the ease in which one can overpressurize the garment and cause restriction of the respiratory process, acidosis or ischemic injury (where the garment presses the skin against underlying bone). A standard method of pressure in a CPC is by using a foot-pump, which makes it extremely difficult to maintain a constant pressure for any length of time. Also, the conditions and excitement surrounding an emergency situation, often result in the ambulance crew over-inflating the garment.

Another problem associated with CPC garments is the rapid pressure drop from the accidental puncturing of one or more bladders. A rapid depressurization could be fatal since the victim's blood pressure can decrease by as much as 60 mm Hg.

Pressurized garments are susceptible to temperature and atmospheric pressure changes, forcing the ambulance crew to constantly adjust the garment's pressure. For example, if a skier at the top of a mountain is involved in an accident and is placed in a CPC garment, the pressure within the garment's bladders will change when the skier is brought down to ground level and indoor temperature.

Since the pneumatic pressure fittings are usually metallic, a victim normally cannot be X-rayed for possible fractures while in the garment. Further, the garment usually Cannot be cut away in selected areas to expose portions of the victims body for treatment, as the cutting would open an air bladder and cause depressurization.

SUMMARY OF THE INVENTION

The present invention involves a counterpressure garment which is not dependent on pneumatics to provide the external counterpressure necessary to stabilize the blood pressure of a victim suffering from hypovolemic shock. The garment utilizes a compressible material, like foam, to provide the requisite counterpressure. The suit is applied to the victim's body and is held in place by a fastening means. The fastening means can also be used to compress the material, but usually a separate pressure engagement means is employed. As the foam compresses, it becomes contoured to the shape of the body part underneath and applies pressure to it.

An advantage of this invention over CPC garments is that the danger of over-pressurization is greatly diminished. It is also more durable and safer in other respects. Conventional CPC garments use inflatable bladders which can be punctured, causing a rapid depressurization which may cause a fatal drop in the victim's blood pressure. An ability to resist punctures also allows an attending physician to cut away a portion of the counterpressure garment to attend to a certain part of the victim's body, without having a negative effect on the rest of the garment.

A further advantage of the invention is that it is not subject to temperature and atmospheric changes. For example, the pressure within a conventional CPC garment will increase if it is applied to a victim in cold weather and the victim is then placed inside a warm ambulance or hospital emergency room. Therefore, constant readjustment is required to maintain the original pressure.

Still another object of this invention is to provide a low cost counterpressure garment. In situations where external bleeding must be arrested, it is inevitable that the counterpressure garment will become blood soaked. For hygienic reasons, a disposable garment would be preferred. The costs are prohibitive in making a disposable CPC garment because expensive air-tight bladders and fittings are required.

The foregoing and other objects, features and advantages of this invention will be apparent from the description of the preferred embodiment and the accompanying drawings.

DETAILED DESCRIPTION OF THE INVENTION

Figure 1:
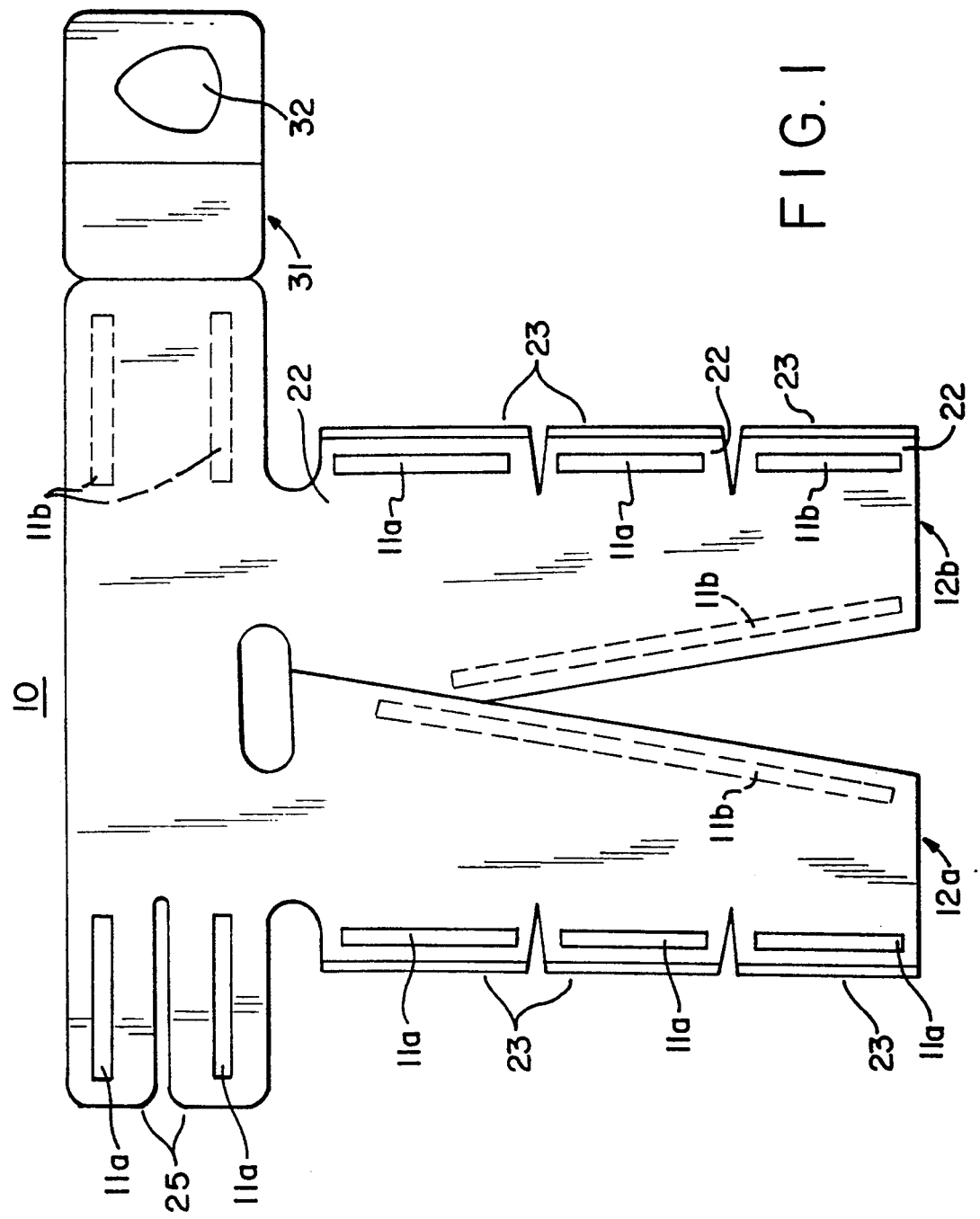
FIG. 1 is a perspective view of the inside of a bladderless counterpressure garment made primarily of foam, utilizing "Velcro" mating strips.

In the drawings, the counterpressure garment is generally designated by 10. In FIG. 1, the garment 10, depicted in a flat position, is adapted to be wrapped about the victim's body and held by an adjustable fastening means. A pair of leg sections 12a, 12b surround the victim's legs. A lower torso section 13 surrounds the victim's abdomen. An adjustable length fastening means 11 is used to secure the garment around the victim and can also provide the requisite counterpressure.

Figure 2:
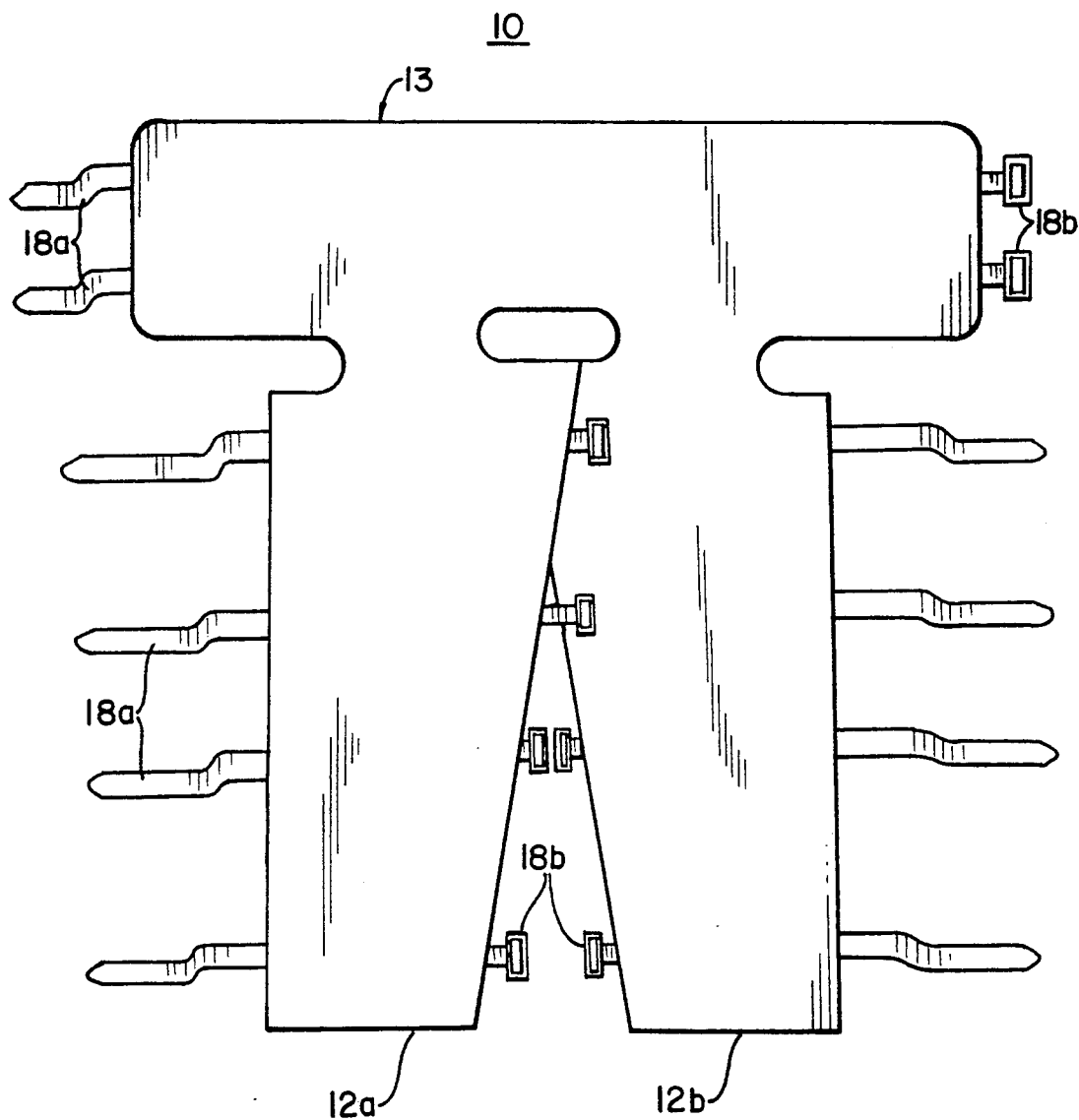
FIG. 2 is a perspective view of the inside of a bladderless counterpressure garment made primarily of foam, utilizing pull-straps.

The garment 10 is made primarily of a compressible material, such as foam. Preferably, a cloth or fabric is used to cover the foam on both inside and outside faces, making a "sandwich". The adjustable length fastening means may be the "VELCRO" mating strips 11a and 11b of FIG. 1, or the pull-straps 18a and buckles 18b of FIG. 2, although any fastening means can be used to secure the garment, including zippers, buttons, snaps and the like. The dashed lines in FIG. 1 indicate that the mating strips 11b are placed on the underside of the garment as depicted.

In the preferred embodiment of FIG. 1, the fastening means, on each leg section, are multiple strips of "VELCRO" attached to leg flaps 22. This allows better control of the counterpressure and an improved fit for each individual wearer. A hand grip 23 connected to the end of the flap allows for a better grip when applying the garment to the wearer. The hand grip can be formed by sewing fabric around a strip of batting cord.

The selection of a compressible material is required so that when applying the fastening means, a range of pressure placed upon the compressible material does not significantly effect the counterpressure applied to the victim. For example, if a 35 lb. application to the pull-straps is needed for the required counterpressure, a 30 to 40 lb. application will not bring the counterpressure applied to the victim out of the beneficial range. (The beneficial range is the range where the victim benefits from the application of the counterpressure garment, i.e. the counterpressure is not so insignificant such that the application of the garment does not increase the blood supply to the victim's vital organs, or not so great as to cause further injury to the victim.) Thus, the inherent properties of the compressible material eliminates the strength of the attendant as a variable in determining the counterpressure applied to the victim.

The number of "VELCRO" mating strips or pull-straps is proportional to the counterpressure applied to the victim. Fine ranges of counterpressure can be achieved by increasing the number of "VELCRO" mating strips or pull-straps. Also, a greater number of "VELCRO" mating strips or pull-straps decreases the effort needed to achieve an equivalent counterpressure. For example, if two (2) pull-straps are used and the needed counterpressure requires a 30–40 lb. application to set each pull-strap, then by increasing the number of pull-straps to four (4) would decrease the pressure needed to set the pull-straps to 15-20 lbs. each.

In another embodiment of the present invention (FIGS. 3 and 4), the fastening means 11a, 11b is used solely to hold the garment about the victim. A separate pressure engagement means is used to set the needed counterpressure. A zipper 14 in each leg section is the preferred type of fastener to be utilized as the pressure engagement means, but any fastener which can compress the material and hold it in place can be used. A zipper allows a more gradual increase in counterpressure than either the "VELCRO" strips or the pull-straps. This method gives the finest gradient for controlling the counterpressure, and also helps in eliminating the strength of the attendant who applies the garment as a variable in setting the counterpressure.

To achieve greater counterpressure about the abdomen, a removable stiffener plate or plates can be situated in the upper section. The stiffener plate can be made of a thick foam or a thin piece of metal. In the preferred embodiment, exhibited in FIG. 1, an abdomen flap 31 can be used to secure a contoured stiffener plate 32. Pockets 17 can also be sewn into the exterior of the lower torso section to secure the stiffener plates 16 (See FIG. 4).

Sizing adjustments are inherent in the present invention. Abdomen flaps 25 on the lower torso section allow the counterpressure garment to be adjusted to a particular victim. Leg flaps 22 serve the same purpose. Other sizing adjustments can be made by properly situating the contoured stiffener plate 32 over the victim's stomach. An excess of fabric is designed into the abdomen flap 31 which permits this sizing adjustment. This allows the counterpressure to be applied to the appropriate point of the victim's abdomen. Also, additional fasteners can be placed in the material to aid in sizing each section to the victim. For example, if an additional zipper is used as a sizing means, it can be left open or unzipped when the victim is a large person, and closed or zipped when the victim is smaller. Further, the fastening means can be used to adjust the size for the individual victim, by using wide mating strips of "Velcro".

Figure 3:
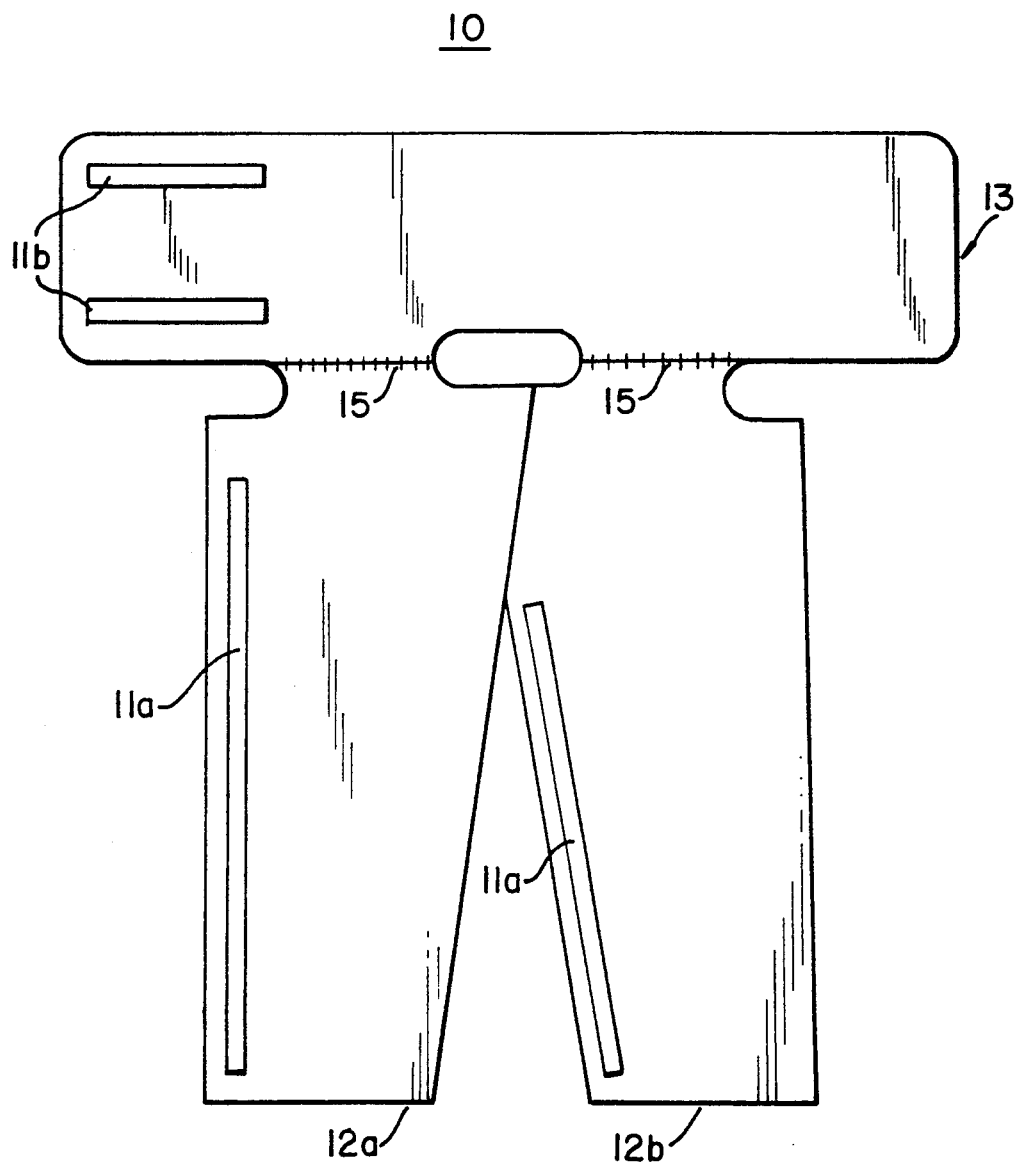
FIG. 3 is a perspective view of the inside of a bladderless counterpressure garment made primarily of foam, and having a separate pressure engagement means.
Figure 4:
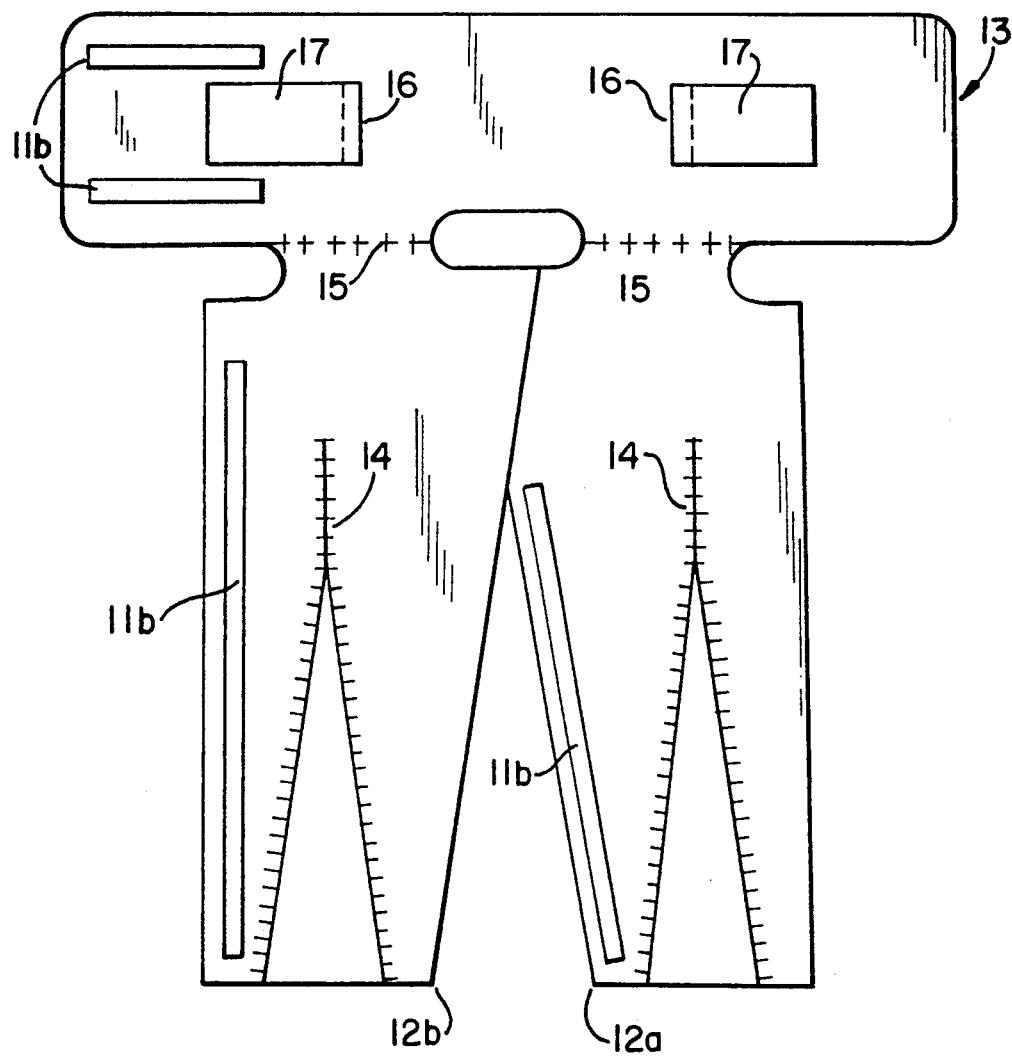
FIG. 4 is a perspective view of the outside of a bladderless counterpressure garment made primarily of foam, and having a separate pressure engagement means.

Any section can be used independently from another section by not engaging the pressure engagement means or by providing a detachable interconnecting means between each lower section and the upper section. If a detachable interconnecting means is desired, the greatest flexibility is achieved by using zippers 15, as shown in FIGS. 3 and 4. "VELCRO" mating strips would also be suitable as a detachable interconnecting means.

The structural strength of foam allows the foam counterpressure garment to be used as a splint. For example, if a broken bone, sprain, or torn ligaments are present, the counterpressure garment can be used to restrict movement and provide the necessary support of the affected area.

There are many variations in which one skilled in the art can adapt the preferred embodiment to suit their particular needs. One variation would be to manufacture a suit which utilizes compressible material (e.g., foam) and resilient material (e.g., elastic) in one suit. This combination foam/elastic counterpressure garment may have advantages over a counterpressure suit made of only one of the aforementioned materials. Other variations include adding one or more inflatable bladders to each section, or substituting buttons or snaps as the primary fastener.

I claim:

1. A counterpressure garment comprising:
   a pair of leg sections for applying around a portion of the legs of a wearer, including the thigh and/or calf sections, and constructed at least partially of a compressible non-inflatable material;
   a lower torso section connected to said pair of leg sections for applying around the lower torso and abdomen of a wearer, and constructed at least partially of a compressible non-inflatable material;
   an adjustable length fastening means for each of said sections, used to secure and to compress the compressible non-inflatable material about the wearer's body; and
   said compressible material being foam.

2. The counterpressure garment of claim 1 wherein the adjustable length fastening means are "VELCRO" mating strips.

3. The counterpressure garment of claim 1 wherein the adjustable length fastening means are pull-straps.

4. The counterpressure garment of claim 1 wherein the adjustable length fastening means is a zipper.

5. The counterpressure garment of claim 1 wherein the adjustable length fastening means for each leg section consists of at least one flap attached to a "VELCRO" mating strip.

6. The counterpressure garment of claim 5 wherein a hand grip is attached to each flap to assist in engaging the fastening means.

7. The counterpressure garment of claim 1 having a means for detachably connecting the lower sections to the upper section.

8. A counterpressure garment comprising:
a pair of leg sections for applying around the legs of the wearer, and constructed at least partially of a compressible material;
a lower torso section connected to said pair of leg sections, dimensioned to be applied around the abdomen of the wearer, and constructed at least partially of a compressible material;
an adjustable length fastening means used to secure the garment about the wearer's body;
a pressure engagement means used to compress the compressible material about the wearer's body; and
wherein said compressible material is foam.

9. The counterpressure garment of claim 8 wherein the pressure engagement means are zippers.

10. The counterpressure garment of claim 8 wherein the pressure engagement means are "VELCRO" mating strips.

11. A method of applying external counterpressure to the legs and abdomen of a wearer, which comprises the steps of:
(a) placing a compressible non-inflatable foam material about the legs and abdomen of a wearer; and
(b) securing the compressible non-inflatable foam material about the wearer's body in such a manner that the material is compressed and applies counterpressure to the wearer's body.

12. A method of applying external counterpressure to the legs and abdomen of a wearer, which comprises the steps of:
(a) placing a compressible non-inflatable foam material about the legs and abdomen of a wearer;
(b) securing the compressible non-inflatable foam material about the wearer's body; and
(c) gradually compressing the material about the wearer's body.

* * * * *